United States Patent
Cross

[19]

[11] Patent Number: 6,045,540

[45] Date of Patent: Apr. 4, 2000

[54] FILTRATION APPARATUS

[76] Inventor: David Edward Cross, Hedge End, Hurst Road, East Preston, West Sussex BN16 3AP, United Kingdom

[21] Appl. No.: 09/201,433

[22] Filed: Nov. 30, 1998

[30] Foreign Application Priority Data

Nov. 29, 1997 [GB] United Kingdom .................. 9725192

[51] Int. Cl.[7] .............................. A61M 5/00; B67D 5/58
[52] U.S. Cl. ...................................... 604/256; 222/189.06
[58] Field of Search ................................... 604/256, 246; 222/96, 189.06, 491, 494

[56] References Cited

U.S. PATENT DOCUMENTS

| | | | |
|---|---|---|---|
| 1,963,080 | 6/1934 | Featherstone | 23/258 |
| 3,938,513 | 2/1976 | Hargest | 128/218 R |
| 4,389,314 | 6/1983 | Petretti | 210/241 |
| 5,174,892 | 12/1992 | Davis | 210/131 |
| 5,836,484 | 11/1998 | Gerber | 222/494 |
| 5,858,007 | 1/1999 | Fagan et al. | 604/256 |

FOREIGN PATENT DOCUMENTS

| | | |
|---|---|---|
| 0 267 783 A2 | 5/1988 | European Pat. Off. . |
| 0 640 371 A1 | 3/1995 | European Pat. Off. . |
| 408080 | 4/1934 | United Kingdom . |
| 2197220A | 5/1988 | United Kingdom . |
| 2279233A | 1/1995 | United Kingdom . |
| 2285438A | 7/1995 | United Kingdom . |
| 2302498A | 1/1997 | United Kingdom . |

*Primary Examiner*—Wynn Wood Coggins
*Assistant Examiner*—Sharon Finkel
*Attorney, Agent, or Firm*—Davis and Bujold

[57] ABSTRACT

Filtration apparatus suitable for use as a bladder evacuator includes a hinged, perforate flap 4 that is resiliently biased to extend across an opening 8 through the neck 7 of a squeezable bottle 1 for filtering out solids from liquid discharged when the bottle 1 is squeezed. Return of the liquid when the bottle 1 is released deflects the perforate flap 4 away from the opening 8 against the bias to allow solids to enter the bottle 1 with the returning liquid. A hinged imperforate flap 5 overlies the perforate flap 4 to be deflected with it by the returning liquid, but separates from it across the opening 8 when the bottle 1 is squeezed. The two flaps 4,5 are part of a folded sheet that is clamped onto a rim 6 of the bottle-neck 7 under a shoulder 12 of the bottle-cap 2; the shoulder 12 holds the perforate flap 4 against deflection away from the opening 8 when the bottle 1 is squeezed. As an alternative to a bottle, a squeeze-bulb 20 coupled to a cylinder 21 may be used with a single, perforate flap 24.

13 Claims, 3 Drawing Sheets

FILTRATION APPARATUS

This invention relates to filtration.

The invention is concerned in particular, though not exclusively, with apparatus for filtration of a kind suitable as a medical evacuator for use in urology.

BACKGROUND OF THE INVENTION

The removal of tissue from the prostate gland or from tumours within the bladder is a common urological procedure. It is normally carried out through the urethra using a slender metal instrument which allows the urological surgeon to see the inside of the urethra or bladder. The surgeon can perform a number of procedures using special instruments which are inserted through a specially designed channel within the instrument. Such procedures for removing prostate tissue or bladder tumours are known as trans-urethral resection of the prostate (TURP) or trans-urethral resection of the bladder (TURB) respectively. The instrument used to remove pieces of tissue from the prostate or tumours from the bladder is called a resectoscope and it commonly uses a loop of wire at the end which cuts through the tissue using electro-surgery. This results in pieces of tissue being cut free which are commonly referred to as "chips" or fragments. The whole procedure of removing these fragments is carried out within a liquid environment of glycine; glycine is chosen for its electrical non-conductivity so that it does not interfere with the electro-surgical process. The fragments are released into the liquid and must be removed along with any blood which may be released as the tissue is cut.

The traditional method of removing the fragments and washing away the blood is by means of an Ellik evacuator. This consists of a glass bulb which has upper and lower chambers with a constriction between the two. The top chamber has an outlet on one side which connects to the sheath of the resectoscope be means of a piece of rubber tubing, and an outlet on the other side to which a rubber bulb is attached. With the apparatus completely filled with liquid, the surgeon compresses the rubber bulb to drive liquid through the resectoscope into the patient's bladder. The bulb is then released to draw the liquid back from the bladder bringing with it some of the fragments and blood. The fragments enter the top chamber of the Ellik evacuator with the expectation that they will settle into the lower chamber before the bulb is compressed again. However the flow of liquid across the top of the chamber tends to create a vortex within the glass chambers and this can result in some of the fragments being disturbed and returned to the bladder together with those that may still be in the upper chamber. This is clearly undesirable and results in an inefficient process that requires the evacuator to be emptied at frequent intervals as well as requiring a large number of evacuations to be performed.

Many attempts have been made to improve on the Ellik evacuator, but none has proved satisfactory. In one design the evacuator involves an open-ended tube which extends through a screw cap into a compressible bottle of plasticised polyvinyl chloride. The tube, which extends nearly half the height of the bottle, has a large number of holes through its wall so that when the bottle is squeezed, liquid is driven through these holes as well as through the larger open-end of the tube, to be expelled from the tube into the sheath of the resectoscope and thence into the bladder. As the bottle is released, the liquid returns from the bladder bringing some of the fragments with it, and these fragments which in general cannot pass through the holes, pass into the bottle from the open end of the tube. The intention is that the fragments should settle to the bottom of the bottle, and that when the bottle is subsequently compressed fragments that have not settled will be filtered out as the liquid containing them passes through the holes in the tube-wall. However, there is nothing in this form of apparatus to prevent fragments from entering the open end of the tube and so be returned to the bladder via the resectoscope.

SUMMARY OF THE INVENTION

It is one of the objects of the present invention to provide apparatus for filtration that enables greater efficiency and simplicity to be achieved in the provision of, for example, a medical evacuator for use in urology.

According to the present invention there is provided filtration apparatus comprising means which defines a chamber having an opening for liquid flow into and out of the chamber, and which is operable for successively drawing liquid into, and discharging it from, the chamber through the opening, and a perforate flap for extending across the opening for filtering solids from the liquid when discharged from the chamber through the opening, the flap being hinged with resilient bias to urge it into a position in which it extends across the opening as aforesaid and is deflectable away from that position against said bias by the liquid drawn into the chamber through said opening so that solids carried with that liquid may enter the chamber through the opening.

The perforate flap may be formed as a disk with perforations therethrough, but may also be perforate (in the general sense with which this word is used herein, including in the claims) to perform the filtering function specified, by virtue of involving, for example, one or more elements of mesh or microporous medium.

An imperforate flap may overlie the perforate flap across the opening. It may be hinged for deflection away from across the opening with the perforate flap by the liquid drawn into the chamber through the opening, but to be deflected in the opposite direction, away from across the opening and the perforate flap, in response to discharge of the liquid through the perforate flap.

The chamber may be the interior of a bottle with the opening in a neck of the bottle. The perforate flap may then be hinged to a member which seats on an annular rim of the neck and which is clamped to it by a cap that screws on the neck. The cap may have an annular shoulder that projects inwardly for obstructing deflection of the perforate flap outwardly of the chamber through the opening, and in this case the member to which the perforate flap is hinged may be clamped to the annular rim between this shoulder and the rim.

The filtration apparatus of the invention may be used as a medical evacuator, for example, in TURP or TURB. In this context the chamber may conveniently be the interior of a bottle having a flexible wall or involve a flexible bulb, the bottle or bulb being of a form that can be grasped in the hand to enable liquid to be successively discharged from and drawn back into the container through the opening by first squeezing and then releasing the bottle or bulb in the hand.

BRIEF DESCRIPTION OF THE DRAWINGS

Medical evacuators according to the present invention, suitable for use in TURP or TURB, will now be described, by way of example, with reference to the accompanying drawings, in which.

DESCRIPTION OF THE PREFERRED EMBODIMENTS

Figure 1:
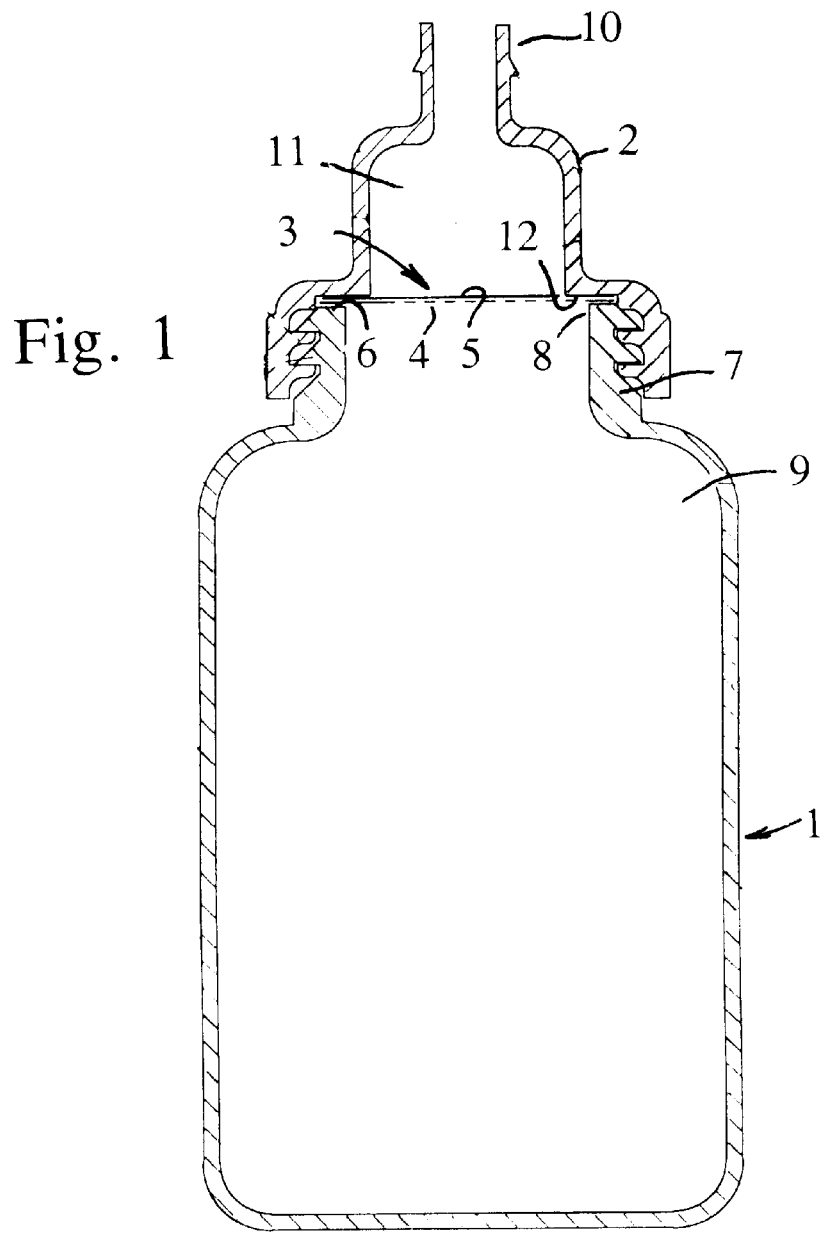
FIG. 1 is a cross-sectional view of a first of the medical evacuators of the invention.

Referring to FIG. 1, the evacuator comprises a bottle 1 having a screw-cap 2, and a flap-valve 3 having perforate and imperforate flaps 4 and 5 respectively. The bottle 1 is of a polymeric material (such as plasticised polyvinyl chloride) or rubber, enabling it to be squeezed by hand to compress the bottle 1 and to return resiliently to its original shape when compression is released. The flap-valve 3 is seated on the annular rim 6 of the threaded neck 7 of the bottle 1 so as to extend across the opening 8 to the bottle-interior 9 under the cap 2 screwed to the neck 7.

The screw-cap 2, which is moulded from a polymeric material such as high density polyethylene, has a tubular outlet 10 for connection to a resectoscope (not shown). The outlet 10 leads from a cylindrical cavity 11 within the cap 2 that is smaller in diameter than the neck-opening 8 so as to create an annular ledge or shoulder 12 that projects inwardly of the opening 8. The shoulder 12 of the screwed-down cap 2 clamps the flap-valve 3 down onto its seating on the rim 6 of the neck 7.

Figure 2:
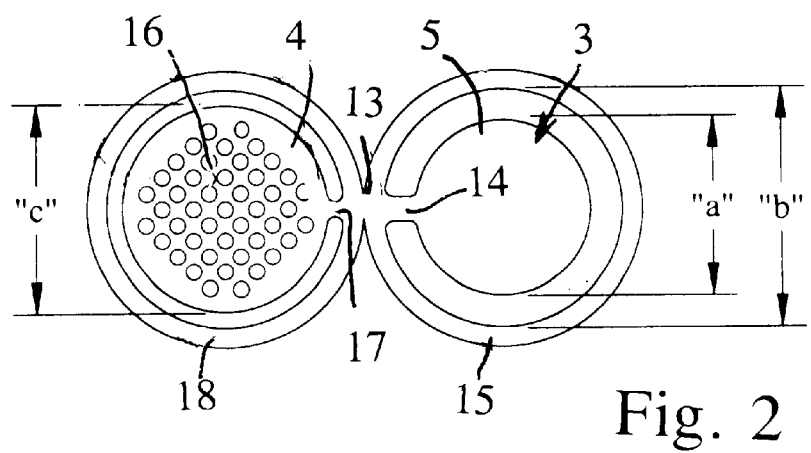
FIG. 2 is illustrative of the construction of a flap valve of the medical evacuator of FIG. 1, the flap valve being shown in the form of a stamping ready for folding before installation in the evacuator.

Referring to FIG. 2, the flap-valve 3 including the perforate and imperforate flaps 4 and 5, is stamped out of thin sheet material (such as polyester film having a thickness of 0.1 mm) preferably in one piece as shown. The flaps 4 and 5 are defined within two circular portions of the stamping that are interconnected at a part 13. One of the sheet-portions is cut to define the imperforate flap 5 of diameter 'a', joined by a tongue 14 to a surrounding annular frame-element 15 of internal diameter 'b'. The flap 4 having perforations 16 and of diameter 'c' larger than 'a', is cut from the other sheet-portion, with a tongue 17 joining it to a surrounding annular frame-element 18 of internal diameter 'b'. The tongues 14 and 17 act as flexible hinges to allow the flaps 5 and 4 to be deflected resiliently up or down from within their frame-elements 15 and 18.

The flap-valve 3 is installed during assembly of the evacuator, by first folding the two circular portions of the sheet-stamping of FIG. 2, one upon the other, and locating the superposed frame-elements 15 and 18 on the bottle-neck 7 with the frame-element 18 facing downwardly onto the rim 6; the internal diameter 'b' of each frame-element 15 and 18 is substantially the same as that of the opening 8 so that they both seat on the rim 6 directly in register with it. The bottle-cap 2 is now screwed onto the neck 7 bringing the shoulder 12 firmly down onto the frame-element 15 to clamp the flap-valve 3 tightly across the opening 8 onto the rim 6.

The diameter 'c' of the perforate flap 4 is larger than the internal diameter of the shoulder 12 but slightly smaller than the internal diameter of the bottle-neck 7 so that although the flap 4 can be deflected downwardly about its hinge-tongue 17 into the bottle 1 it is precluded by the shoulder 12 from being deflected upwardly out of the bottle-neck opening 8. However, the imperforate flap 5 is of diameter 'a' smaller than the internal diameter of the shoulder 12 so, being on top of the flap 4, can be deflected about its hinge-tongue 14 both downwardly with the flap 4 into the bottle 1 and upwardly independently of it into the cap 2.

Figure 3:
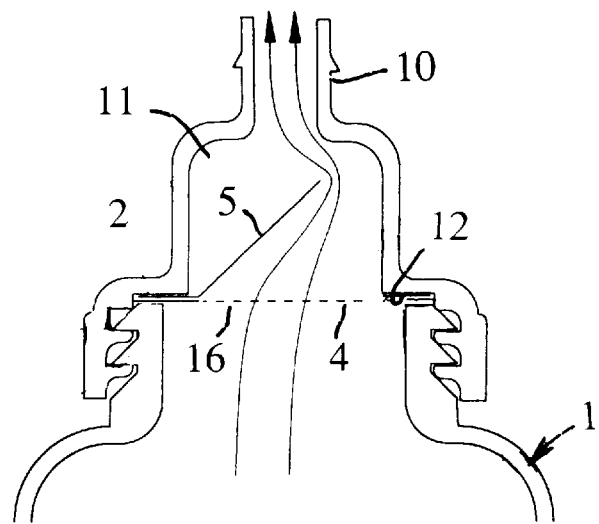
FIG. 3 is an enlarged cross-sectional view of the neck and cap of a bottle forming part of the medical evacuator of FIG. 1, and provides illustration of discharge of liquid from the bottle.

In preparation of the assembled evacuator for use, it is placed in a bowl of sterile glycine and the bottle 1 is repeatedly compressed and released by hand so as to expel air and fill the chamber-interior 9 of the bottle 1 and the cavity 11 of the screw-cap 2 with glycine. The tubular outlet 10 of the evacuator is then connected to the resectoscope as already positioned within the urethra, by rubber tubing (not shown). The surgeon then grasps the bottle 1 by hand and compresses it to drive glycine from the bottle 1 into the resectoscope and thence into the patient's bladder via the outlet 10 of the cap 2; this condition is illustrates in FIG. 3. The flap 4, which owing to the resilience at the hinge-tongue 17 normally adopts the position (shown in FIG. 1) in which it extends across the bottle-neck opening 8, is urged hard against the shoulder 12 by the liquid pressure to remain in that position. The flap 5, however, is deflected upwardly by the pressure into the cavity 11 of the cap 2 so as to be clear of the perforations 16 and enable flow of liquid from the bottle 1 through the flap 4.

Figure 4:
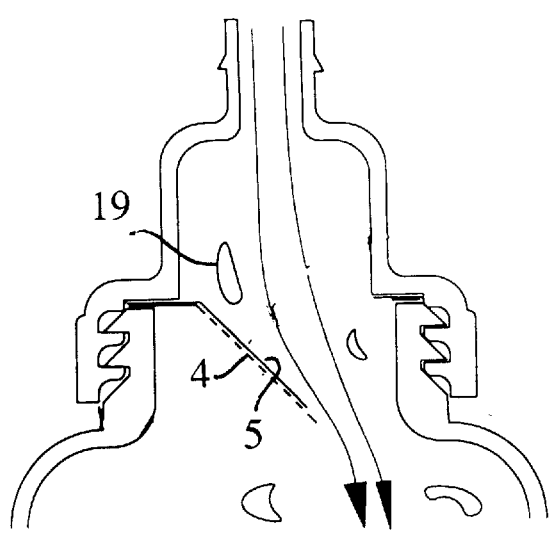
FIGS. 4 and 5 are both enlarged cross-sectional views corresponding to that of FIG. 3, and providing illustration of successive stages of operation of the apparatus of FIG. 1 following the discharge of liquid represented in FIG. 3, FIG. 4 illustrating the drawing of the liquid into the evacuator and FIG. 5 the following return discharge of the liquid from the evacuator.

Release of compression of the bottle 1 allows it to restore resiliently to its normal shape and causes the liquid to be sucked back into the bottle 1. As shown in FIG. 4, the liquid sucked back carries with it debris or fragments 19 resulting from the surgical operation within the bladder or prostate. The suction returns the flap 5 to lie over the flap 4 and block the perforations 16, and draws the flaps 4 and 5 downwardly together so as to enable free flow of the liquid and the fragments 19 carried with it, into the bottle 1.

Figure 5:
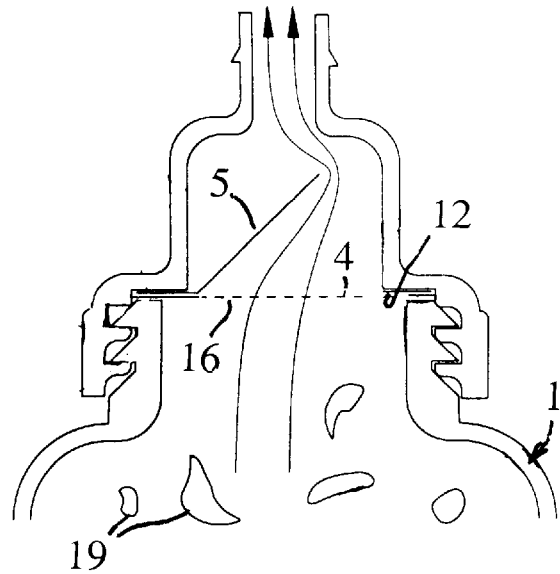

When the bottle 1 is compressed again to return the liquid to the bladder through the resectoscope, the flaps 4 and 5 will usually have already returned under the resilience of their hinge-tongues 14 and 17 to their normal positions across the bottle-neck opening 8. The pressure exerted on the liquid within the interior 9 of the bottle 1, in any case urges the flap 4 upwardly into abutment with the shoulder 12 to hold it firmly there, and deflects the flap 5 upwardly into the cap 2 clear of the flap 4; this is illustrated in FIG. 5. The upward deflection of the flap 5 allows free flow of the liquid from the bottle 1 through the perforations 16 of the flap 4. Fragments 19 which are carried to the perforate flap 4 with the liquid are filtered out so as to remain within the bottle 1, each perforation 16 having a diameter which in this respect is too small to pass the fragments 19 but not so small as to restrict significantly the flow of liquid through them; a diameter of about 2 mm has been found satisfactory.

The operation of the evacuator when compression of the bottle 1 by hand is again released, and then when released thereafter within successive cycles of squeezing and release, is to admit further fragments 19 carried by the liquid to the bottle 1 as the flaps 4 and 5 are deflected downwardly. When the bottle 1 is squeezed again during each cycle, the liquid is driven from the bottle 1 through the perforations 16, leaving the fragments 19 behind trapped by the flap 4 to accumulate in the bottle 1.

The specific form of evacuator as described above has been found to work extremely effectively. Other constructions using the same principle are possible. For example, the perforate and imperforate flaps 4 and 5 could be discrete components. Also, it is possible to arrange for the surrounding frame-element 15 of the imperforate flap 5 to act as a shoulder (instead of the shoulder 12) preventing the perforate flap 4 from entering the cavity 11 of the screw-cap 2. Moreover, the perforate and imperforate flaps 4 and 5 need not be constructed integrally with their surrounding frame-elements 18 and 15, but each could be a discrete disk hinged within a suitable retaining cage.

Furthermore, the evacuator of FIG. 1 may be readily modified to omit the imperforate flap 5. The perforations 16 of the perforate flap 4 in this case, are chosen to be of a diameter sufficiently small to create a back pressure to the liquid flow that is greater than the pressure required to deflect the flap 4 downwardly from across the bottle-neck opening 8. In this way the perforate flap 4 opens to allow both liquid and fragments to enter the bottle 1 but acts as a filter, as in the construction of FIG. 1, to prevent fragments from leaving the bottle 1 in the flow of liquid to the bladder.

Figure 6:
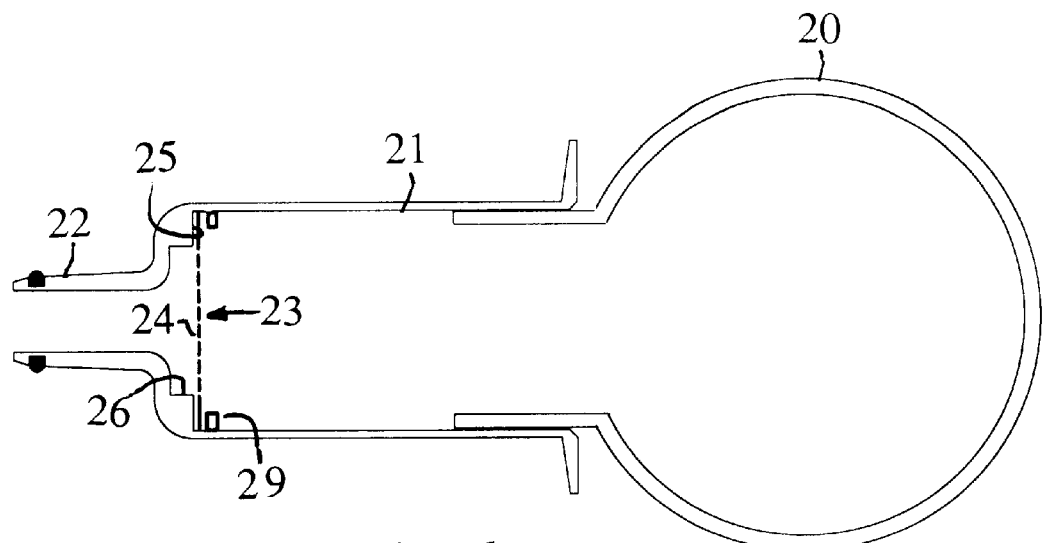
FIG. 6 is a cross-sectional view of the second medical evacuator of the invention.

An alternative form of bladder evacuator utilising a single, perforate flap is illustrated in FIG. 6 and will now be described.

Referring to FIG. 6, a rubber squeeze-bulb 20 is coupled to a cylinder 21 that has a nozzle outlet 22 for connection to the resectoscope; the bulb 20 and cylinder 21 together define the chamber for receiving and discharging the glycine in this case. A flap-valve 23 that has a single perforate flap 24 is held within the cylinder 21 against an annular shoulder 25 to extend across the opening 26 to the nozzle outlet 22 for filtering the liquid during its discharge therethrough.

Figure 8:
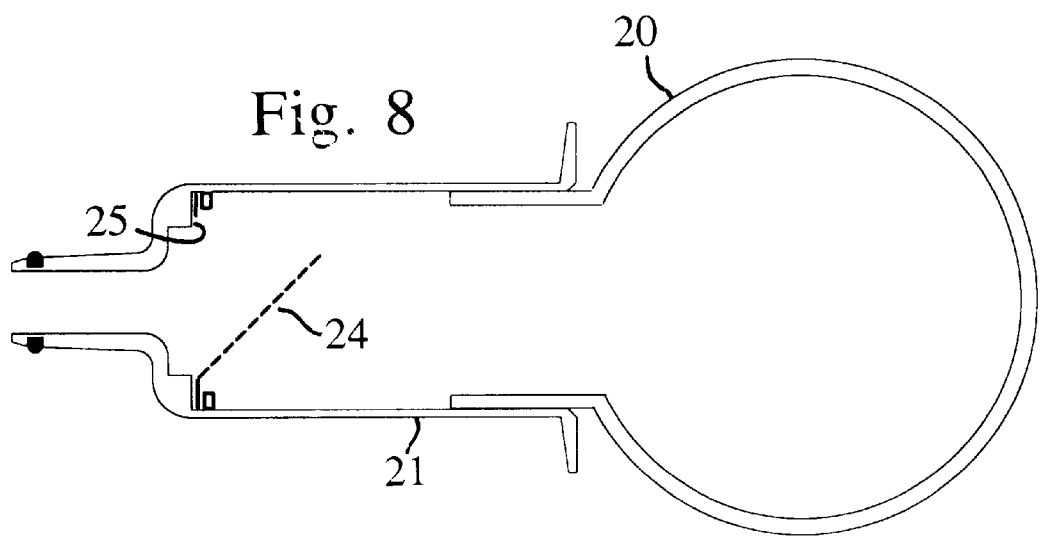
FIG. 8 is a view corresponding to FIG. 6 showing the perforate flap deflected from its normal position.
Figure 7:
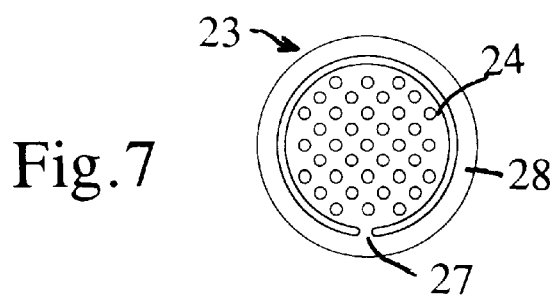
FIG. 7 is illustrative of a perforate flap forming part of the evacuator of FIG. 6.

The flap-valve 23 is formed as illustrated in FIG. 7 as a thin-sheet stamping that is cut to define the perforate flap 24 joined by a tongue 27 to a surrounding annular frame-element 28. As shown in FIG. 6, the frame-element 28 is held tightly against the shoulder 25 by an interference-fit ring 29 and the flap 24 is biassed by the resilience of the hinge-tongue 27 to abut the shoulder 25. The flap 24 remains in this condition when the bulb 20 is squeezed to expel the liquid from the cylinder 21 through the perforate flap 24, but hinges through the ring 29 as illustrated in FIG. 8 while the liquid is being drawn back into the cylinder 21 on release of the bulb 20. The resilience of the hinge-tongue 27 ensures that the flap 24 returns to its normal position across the opening 26 to the nozzle 22 for filtration purposes, when the return flow ends and prior to further squeezing of the bulb 20.

I claim:

1. Filtration apparatus comprising: means defining a chamber having an opening for liquid flow into and out of the chamber, said means being selectively operable for successively permitting one of a decreased and increased pressure within said chamber for respectively drawing liquid into, and discharging it from, the chamber through the opening; a perforate flap for extending across the opening for filtering solids from the liquid when discharged from the chamber through the opening, said flap having perforations therethrough for passing liquid through the flap whilst blocking solids from passing through; and hinge means mounting the perforate flap for angular displacement from an operative position in which said flap extends across the opening as aforesaid to a position in which said flap is angularly deflected away from the opening for admitting solids to the chamber through the opening, said hinge means comprising means providing resilient bias for returning said flap to its operative position and means mounting said flap to be angularly displaced from the operative position against said bias by liquid drawn into the chamber through the opening.

2. Filtration apparatus according to claim 1 wherein the flap is of sheet-form, and the hinge means comprises an element surrounding the flap and a tongue interconnecting said element and flap.

3. Filtration apparatus according to claim 2 wherein the flap and surrounding element interconnected by the tongue are of a unitary construction.

4. Filtration apparatus according to claim 1 wherein said means defining the chamber involves a flexible element that is deflectable for applying pressure within the chamber to urge the liquid to be discharged from the chamber through the opening.

5. Filtration apparatus according to claim 1 including an imperforate flap, and hinge means mounting the imperforate flap to overly the perforate flap across the opening for deflection in one direction away from across the opening with the perforate flap by liquid drawn into the chamber through the opening, and in the opposite direction away from across the opening and the perforate flap in response to discharge of liquid from the chamber through the perforate flap.

6. Filtration apparatus according to claim 5 wherein the perforate and imperforate flaps are parts of a unitary flexible sheet, the sheet having first and second portions each of which comprises a flap-forming element, a frame-element surrounding the flap-forming element and means hinging the flap-forming element within its surrounding frame-element, the flap-forming elements of the first and second portions are perforate and imperforate respectively, and the first and second portions of the sheet are folded over one another with the flap-forming element of the second portion overlying the flap-forming element of the first portion.

7. Filtration apparatus according to claim 1 wherein the means defining the chamber comprises a cylinder having a hand-squeezable bulb and an outlet nozzle, and the perforate flap is mounted within the cylinder adjacent the outlet nozzle.

8. Filtration apparatus comprising: means defining a chamber having an opening for liquid flow into and out of the chamber, said means being selectively operable for successively drawing liquid into, and discharging it from, the chamber through the opening; a perforate flap extending across the opening for filtering solids from the liquid when discharged from the chamber through the opening; and hinge means for mounting the flap for angular displacement from an operative position in which the flap extends across the opening as aforesaid to a position in which the flap is deflected away from the opening for admitting solids to the chamber through the opening, said hinge means comprising means providing resilient bias for returning the flap to its operative position and means mounting the flap to be angularly displaced from the operative position against said bias by liquid drawn into the chamber through the opening; said means defining the chamber comprising a bottle having a neck with an open top surrounded by an annular rim of the neck, said hinge means comprising a member for seating on the rim to locate the perforate flap across the open top of the neck, and said apparatus further including a cap that screws on the neck to clamp said member to said rim.

9. Filtration apparatus according to claim 12 wherein the cap has an internal projection for obstructing deflection of the perforate flap into the cap from the open top.

10. Filtration apparatus according to claim 9 wherein said projection is an annular shoulder of the cap that projects inwardly of the cap, and said member is clamped to the annular rim between this shoulder and the rim.

11. Filtration apparatus according to claim 8 wherein the bottle has a flexible wall for grasping in the hand to enable liquid to be successively discharged from and drawn back into the bottle through the opening by first squeezing and then releasing the bottle in the hand.

12. Bladder-evacuator apparatus comprising: a flexible-walled bottle having an opening for liquid flow into and out of the bottle, the bottle being hand-squeezable for successively drawing liquid into, and discharging it from the bottle through the opening; a perforate flap for extending across the opening to filter solids from liquid discharging from the bottle through the opening, said flap having perforations therethrough for passing the liquid through the flap whilst blocking the solids from passage therethrough; and hinge means for mounting the perforate flap for angular displacement from an operative position in which said flap extends across the opening as aforesaid to a position in which said flap is angularly deflected away from the opening for admitting solids to the bottle through the opening, said hinge means comprising means providing resilient bias for returning said flap to said operative position and means mounting said flap to be angularly displaced from the operative position against said bias by liquid drawn into the bottle through the opening.

13. Bladder-evacuator apparatus according to claim 12 including an imperforate flap, and further hinge means for hinging said imperforate flap to overly said perforate flap across said opening for deflection in one direction away from across said opening with said perforate flap by liquid drawn into the bottle through said opening, and in the opposite direction away from across said opening and said perforate flap in response to discharge of liquid from the bottle through said perforate flap.

* * * * *